United States Patent [19]

Bundy

[11] 4,152,514

[45] May 1, 1979

[54] 9α,5-NITRILO-9-DEOXY-PGF₁ COMPOUNDS

[75] Inventor: Gordon L. Bundy, Portage, Mich.

[73] Assignee: The Upjohn Company, Kalamazoo, Mich.

[21] Appl. No.: 893,584

[22] Filed: Apr. 5, 1978

Related U.S. Application Data

[63] Continuation-in-part of Ser. No. 807,514, Jun. 17, 1977, Pat. No. 4,097,489.

[51] Int. Cl.² ........................................... C07D 221/04
[52] U.S. Cl. .................... 542/426; 546/183; 546/112; 424/256; 542/421; 542/422; 542/416; 542/427; 542/429
[58] Field of Search ........................ 260/295 F, 294.9; 542/426, 429, 427, 421, 416, 422

[56] References Cited

U.S. PATENT DOCUMENTS

| | | | |
|---|---|---|---|
| 3,931,289 | 1/1976 | Bundy | 260/473 A |
| 3,983,157 | 9/1976 | Bundy | 260/473 A |
| 3,983,178 | 9/1976 | Bundy | 260/473 A |

*Primary Examiner*—Arthur P. Demers
*Attorney, Agent, or Firm*—Robert A. Armitage

[57] ABSTRACT

This invention relates to certain structural and pharmacological analogs of prostacyclin (PGI₂) wherein a nitrogen atom is substituted for the 6,9α-epoxy-oxygen of prostacyclin. These novel nitrogen-containing prostacyclin-type compounds are useful for the pharmacological purposes for which prostacyclin is used, e.g., as antithrombotic agents, antihypertensive agents, antiasthma agents, nasal decongestants, or regulators of fertility and procreation.

47 Claims, No Drawings

9α,5-NITRILO-9-DEOXY-PGF₁ COMPOUNDS

CROSS REFERENCE TO RELATED APPLICATION

This application is a continuation-in-part of Ser. No. 807,514, filed June 17, 1977, now U.S. Pat. No. 4,097,489, issued June 27, 1978.

The present invention relates to prostacyclin analogs, the essential material constituting a disclosure thereof is incorporated here by reference from Ser. No. 807,514, filed June 17, 1977 now U.S. Pat. No. 4,097,489 issued June 27, 1978.

The present invention specifically relates to the following prostacyclin analogs:

(a) 9,11-Dideoxy-11α-hydroxymethyl-9α,5-nitrilo-PGF₁;
(b) 9,11-Dideoxy-9α,5-nitrilo-PGF₁;
(c) 9-Deoxy-9α,6-nitrilomethylene-PGF₁;
(d) 9-Deoxy-9α,6-nitrilo-cis-13-PGF₁;
(e) 9-Deoxy-9α,5-nitrilo-13,14-didehydro-PGF₁;
(f) 9-Deoxy-9α,5-nitrilo-14-chloro-PGF₁;
(g) 9-Deoxy-9α,5-nitrilo-13,14-didehydro-PGF₁;
(h) 2,2-Difluoro-9-deoxy-9α,5-nitrilo-15-methyl-PGF₁;
(i) Trans-2,3-didehydro-9-deoxy-9α,5-nitrilo-PGF₁;
(j) 9-Deoxy-9α,5-nitrilo-17-phenyl-18,19,20-trinor-PGF₁;
(k) 9-Deoxy-9α,5-nitrilo-16-phenoxy-17,18,19,20-tetranor-PGF₁;
(l) 9-Deoxy-9α,5-nitrilo-PGF₁, amide;
(m) 2-Decarboxy-2-hydroxymethyl-9-deoxy-9α,5-nitrilo-PGF₁;
(n) 9-Deoxy-9α,5-nitrilo-15-methyl-PGF₁;
(o) 9-Deoxy-9α,5-nitrilo-16,16-difluoro-PGF₁;
(p) 9-Deoxy-9α,5-nitrilo-16,16-dimethyl-PGF₁;
(q) 9-Deoxy-9α,5-nitrilo-PGF₁, methyl ester;
(r) 9-Deoxy-9α,5-nitrilo-PGF₁, tris(hydroxymethyl)amino methane salt;
(s) 9-Deoxy-9α,5-nitrilo-PGF₁, hydrochloride; and
(t) 9-Deoxy-9α,5-nitrilo-PGF₁.

I claim:

1. A prostacyclin analog of the formula

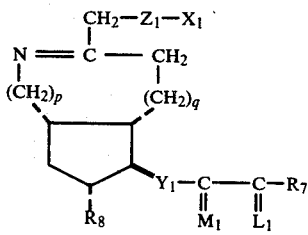

wherein one of p and q is the integer one and the other is the integer zero;
wherein Z₁ is
(1) —(CH₂)$_g$—CH₂—CH₂—,
(2) —(CH₂)$_g$—CH₂—CF₂—, or
(3) trans-(CH₂)$_g$—CH=CH—,
wherein g is the integer zero, one, or 2;
wherein R₈ is hydrogen, hydroxy, or hydroxymethyl;
wherein Y₁ is
(1) trans-CH=CH—
(2) cis-CH=CH—,
(3) —CH₂CH₂—,
(4) trans-CH=C(Hal)—, or
(5) —C≡C— wherein Hal is chloro or bromo;
wherein M₁ is

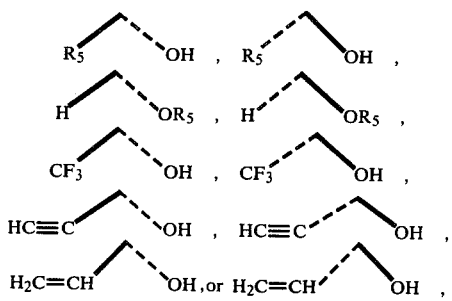

wherein R₅ is hydrogen or alkyl with one to 4 carbon atoms, inclusive,
wherein L₁ is

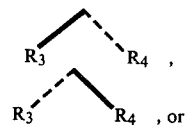

a mixture of

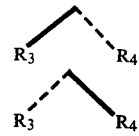

wherein R₃ and R₄ are hydrogen, methyl, or fluoro, being the same or different, with the proviso that one of R₃ and R₄ is fluoro only when the other is hydrogen or fluoro;
wherein X₁ is
(1) —COOR₁ wherein R₁ is hydrogen; alkyl of one to 12 carbon atoms, inclusive; cycloalkyl of 3 to 10 carbon atoms, inclusive, aralkyl of 7 to 12 carbon atoms, inclusive; phenyl; phenyl substituted with one, two, or three chloro or alkyl of one to 3 carbon atoms; phenyl substituted in the para position by

(a)

(b)

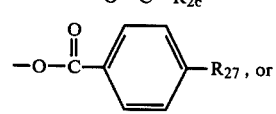
(c)

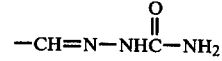
(d)

wherein R₂₅ is methyl, phenyl, acetamidophenyl, benzamidophenyl, or —NH₂; R₂₆ is methyl, phenyl, —NH₂, or methoxy; and R₂₇ is hydrogen or acetamido, inclusive; or a pharmacologically acceptable cation;
(2) —CH₂OH; or
(3) —COL₄, wherein L₄ is (a) amino of the formula —NR₂₁R₂₂, wherein R₂₁ and R₂₂ are
(i) hydrogen;
(ii) alkyl of one to 12 carbon atoms, inclusive;
(iii) cycloalkyl of 3 to 10 carbon atoms, inclusive;

(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy, inclusive, carboxy, alkoxycarbonyl of one to 4 carbon atoms, inclusive, or nitro;
(vii) carboxyalkyl of one to four carbon atoms, inclusive;
(viii) carbamoylalkyl of one to four carbon atoms, inclusive;
(ix) cyanoalkyl of one to four carbon atoms, inclusive;
(x) acetylalkyl of one to four carbon atoms, inclusive;
(xi) benzoylalkyl of one to four carbon atoms, inclusive;
(xii) benzoylalkyl substituted by one, 2, or 3 chloro, alkyl of one to 3 carbon atoms inclusive; hydroxy, alkoxy of one to 3 carbon atoms, inclusive; carboxy, alkoxycarbonyl of one to 4 carbon atoms, inclusive, or nitro;
(xiii) hydroxyalkyl of one to 4 carbon atoms, inclusive;
(xiv) dihydroxyalkyl of one to 4 carbon atoms; and
(xv) trihydroxyalkyl of one to 4 carbon atoms; with the further proviso that not more than one of $R_{21}$ and $R_{22}$ is other than hydrogen or alkyl;
(b) carbonylamino of the formula —$NR_{23}COR_{21}$, wherein $R_{23}$ is hydrogen or alkyl of one to 4 carbon atoms and $R_{21}$ is as defined above;
(c) sulphonylamino of the formula —$NR_{23}SO_2R_{21}$, wherein $R_{21}$ and $R_{23}$ are as defined above; or
(d) hydrazino of the formula —$NR_{23}R_{24}$, wherein $R_{24}$ is amino of the formula —$NR_{21}R_{22}$, as defined above;
wherein $R_7$ is —$(CH_2)_m$—$CH_3$,     (1)

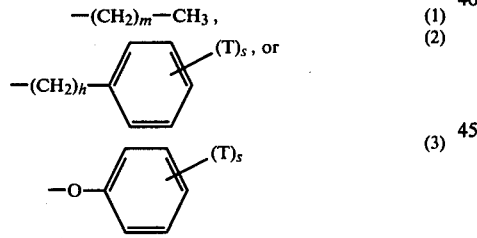

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, or with the proviso that not more than two T's are other than alkyl; and the pharmacologically acceptable acid addition salts thereof when $R_2$ is not alkylcarbonyl and $R_1$ is not a pharmacologically acceptable cation.

2. A prostacyclin analog according to claim 1, wherein $R_8$ is hydroxymethyl.

3. 9,11-Dideoxy-11α-hydroxymethyl-9α,5-nitrilo-$PGF_1$, a prostacyclin analog according to claim 2.

4. A prostacyclin analog according to claim 1, wherein $R_8$ is hydrogen.

5. 9,11-Dideoxy-9α,5-nitrilo-$PGF_1$, a prostacyclin analog according to claim 4.

6. A prostacyclin analog according to claim 1, wherein $R_8$ is hydroxy.

7. A prostacyclin analog according to claim 6, wherein p is one.

8. 9-Deoxy-9α,6-nitrilomethylene-$PGF_1$, a prostacyclin analog according to claim 7.

9. A prostacyclin analog according to claim 6, wherein q is one.

10. A prostacyclin analog according to claim 6, wherein $Y_1$ is cis-CH=CH—.

11. 9-Deoxy-9α,5-nitrilo-cis-13-$PGF_1$, a prostacyclin analog according to claim 10.

12. A prostacyclin analog according to claim 6, wherein $Y_1$ is —C≡C—.

13. 9-Deoxy-9α,5-nitrilo-13,14-didehydro-$PGF_1$, a prostacyclin analog according to claim 12.

14. A prostacyclin analog according to claim 6, wherein $Y_1$ is trans-CH=C(Hal)—.

15. 9-Deoxy-9α,5-nitrilo-14-chloro-$PGF_1$, a prostacyclin analog according to claim 14.

16. A prostacyclin analog according to claim 6, wherein $Y_1$ is —$CH_2CH_2$—.

17. 9-Deoxy-9α,5-nitrilo-13,14-didehydro-$PGF_1$, a prostacyclin analog according to claim 16.

18. A prostacyclin analog according to claim 6, wherein $Y_1$ is trans-CH=CH—.

19. A prostacyclin analog according to claim 18, wherein $Z_1$ is —$(CH_2)_g$—$CH_2$—$CF_2$.

20. 2,2-Difluoro-9-deoxy-9α,5-nitrilo-15-methyl-$PGF_1$, a prostacyclin analog according to claim 19.

21. A prostacyclin analog according to claim 18, wherein $Z_1$ is trans-$(CH_2)_g$-CH=CH—.

22. Trans-2,3-didehydro-9-deoxy-9α,5-nitrilo-$PGF_1$, a prostacyclin analog according to claim 21.

23. A prostacyclin analog according to claim 18, wherein $Z_1$ is —$(CH_2)_g$—$CH_2$-$CH_2$—.

24. A prostacyclin analog according to claim 23, wherein g is zero.

25. A prostacyclin analog according to claim 24, wherein $R_7$ is

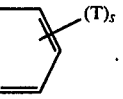

26. 9-Deoxy-9α,5-nitrilo-17-phenyl-18,19,20-trinor-$PGF_1$, a prostacyclin analog according to claim 25.

27. A prostacyclin analog according to claim 24, wherein $R_7$ is

28. 9-Deoxy-9α,5-nitrilo-16-phenoxy-17,18,19,20-tetranor-$PGF_1$, a prostacyclin analog according to claim 27.

29. A prostacyclin analog according to claim 24, wherein $R_7$ is —$(CH_2)_m$—$CH_3$—.

30. A prostacyclin analog according to claim 29, wherein m is 3.

31. A prostacyclin analog according to claim 30, wherein $X_1$ is —$COL_4$.

32. 9-Deoxy-9α,5-nitrilo-$PGF_1$, amide, a prostacyclin analog according to claim 31.

33. A prostacyclin analog according to claim 31, wherein $X_1$ is $CH_2OH-$.

34. 2-Decarboxy-2-hydroxymethyl-9-deoxy-9α,5-nitrilo-PGF$_1$, a prostacyclin analog according to claim 33.

35. A prostacyclin analog according to claim 30, wherein $X_1$ is $-COOR_1$.

36. A prostacyclin analog according to claim 35, wherein $R_5$ is methyl.

37. 9-Deoxy-9α,5-nitrilo-15-methyl-PGF$_1$, a prostacyclin analog according to claim 36.

38. A prostacyclin analog according to claim 35, wherein $R_5$ is hydrogen.

39. A prostacyclin analog according to claim 38, wherein at least one of $R_3$ and $R_4$ is fluoro.

40. 9-Deoxy-9α,5-nitrilo-16,16-difluoro-PGF$_1$, a prostacyclin analog according to claim 39.

41. A prostacyclin analog according to claim 38, wherein at least one of $R_3$ and $R_4$ is methyl.

42. 9-Deoxy-9α,5-nitrilo-16,16-dimethyl-PGF$_1$, a prostacyclin analog according to claim 41.

43. A prostacyclin analog according to claim 38, wherein $R_3$ and $R_4$ are both hydrogen.

44. 9-Deoxy-9α,5-nitrilo-PGF$_1$, methyl ester, a prostacyclin analog according to claim 43.

45. 9-Deoxy-9α,5-nitrilo-PGF$_1$, tris(hydroxymethyl-)amino methane salt, a prostacyclin analog according to claim 43.

46. 9-Deoxy-9α,5-nitrilo-PGF$_1$, hydrochloride, a prostacyclin analog according to claim 43.

47. 9-Deoxy-9α,5-nitrilo-PGF$_1$, a prostacyclin analog according to claim 43.

* * * * *